US008715662B2

(12) United States Patent
Alberti

(10) Patent No.: US 8,715,662 B2
(45) Date of Patent: May 6, 2014

(54) ANTI-TROP-2 MONOCLONAL ANTIBODIES AND USES THEREOF IN THE TREATMENT AND DIAGNOSIS OF TUMORS

(75) Inventor: Saverio Alberti, Chieti Scalo (IT)

(73) Assignee: Oncoxx Biotech S.R.L., Chieti (IT)

( * ) Notice: Subject to any disclaimer, the term of this patent is extended or adjusted under 35 U.S.C. 154(b) by 237 days.

(21) Appl. No.: 13/146,012

(22) PCT Filed: Feb. 5, 2009

(86) PCT No.: PCT/IT2009/000035

§ 371 (c)(1), (2), (4) Date: Nov. 10, 2011

(87) PCT Pub. No.: WO2010/089782

PCT Pub. Date: Aug. 12, 2010

(65) Prior Publication Data

US 2012/0052076 A1 Mar. 1, 2012

(51) Int. Cl.
*A61K 39/395* (2006.01)

(52) U.S. Cl.
USPC .................................... 424/138.1; 530/388.8

(58) Field of Classification Search
None
See application file for complete search history.

(56) References Cited

U.S. PATENT DOCUMENTS

| | | | | |
|---|---|---|---|---|
| 2004/0001825 | A1 | 1/2004 | Govindan et al. | |
| 2007/0212350 | A1 | 9/2007 | Govindan et al. | |
| 2008/0131363 | A1 | 6/2008 | Govindan et al. | |
| 2008/0305104 | A1 | 12/2008 | Young et al. | 424/133.1 |

FOREIGN PATENT DOCUMENTS

| | | |
|---|---|---|
| WO | 98/12227 | 3/1998 |
| WO | 03/074566 | 9/2003 |
| WO | 2007/095748 | 8/2007 |
| WO | 2008/144891 | 12/2008 |

OTHER PUBLICATIONS

Calabrese, G. et al. Assignment of TACSTD1 (alias TROP1, M4S1) to human chromosome 2p21 and refinement of mapping of TACSTD2 (alias TROP2, M1S1) to human chromosome 1p32 by in situ hybridization. Cytogenet. Cell Genet. 92, 164-5 (2001).

Fornaro, M. et al. Cloning of the gene encoding TROP-2, a cellsurface glycoprotein expressed by human carcinomas. Int. J. Cancer 62, 610-8 (1995).

Alberti, S. et al. Biochemical characterization of Trop-2, a cell surface molecule expressed by human carcinomas: formal proof that the monoclonal antibodies T16 and MOv-16 recognize Trop-2. Hybridoma 11, 539-5 (1992).

Fradet, Y., Cordon-Cardo, C., Whitmore, W. F., Jr., Melamed, M. R. & Old, L. J. Cell surface antigens of human bladder tumors: definition of tumor subsets by monoclonal antibodies and correlation with growth characteristics. Cancer Res 46, 5183-8 (1986).

Stein, R., Chen, S., Sharkey, R. M. & Goldenberg, D. M. Murine monoclonal antibodies raised against human non-small cell carcinoma of the lung: specificity and tumor targeting. Cancer Res. 50, 1330-6 (1990).

Linnenbach, A. J. et al. Retroposition in a family of carcinoma associated antigen genes. Mol. Cell. Biol. 13, 1507-1515 (1993).

Ciccarelli, F., Acciarito, A. & Alberti, S. Large and diverse numbers of human diseases with HIKE mutations. Hum. Mol. Genet. 9, 1001-7 (2000).

Basu, A., Goldenberg, D. M. & Stein, R. The epithelial/carcinoma antigen EGP-1, recognized by monoclonal antibody RS7-3G11, is phosphorylated on serine 303. Int. J. Cancer 62, 472-479 (1995).

Velders, M. P. et al. The impact of antigen density and antibody affinity on antibody-dependent cellular cytotoxicity: relevance for immunotherapy of carcinomas. Br.J.Cancer 78, 478-483 (1998).

Johnson, B. E. & Janne, P. A. Rationale for a phase II trial of pertuzumab, a HER-2 dimerization . inhibitor, in patients with nonsmall cell lung cancer. Clin Cancer Res 12, 4436s-4440s (2006).

Oi, V. T., Morrison, S. L., Herzenberg, L. A. & Berg, P. Immunoglobulin gene expression in transformed lymphoid cells. Proc Natl Acad Sci US A 80, 825-9 (1983).

Alberti, S., Nutini, M. & Herzenberg, L. A. DNA methylation prevents the amplification of TROP1, a tumor associated cell surface antigen gene. Proc. Natl. Acad. Sci. USA 91, 5833-7 (1994).

Zanna, P. et al. Trop-1 Are Conserved Growth Stimulatory Molecules That Mark Early Stages of Tumor Progression. Cancer 110, 452-464 (2007).

Garofalo, A. et al. Comparative study on the metastatic behavior of human tumors in nude, beige/nude/xid and severe combined immunodeficient mice. Invasion Metastasis 13, 82-91 (1993).

Wang, Z., et al. Universal PCR amplification of mouse immunoglobulin gene variable regions: the design of degenerate primers and an assessment of the effect of DNA polymerase 3' to 5' exonuclease activity. J. Immunol. Methods 233, 167-177 (2000).

Lefranc, MP. et al. IMGT, the international ImMunoGeneTics information system®: a standardized approach for immunogenetics and immunoinformatics, Immunome Research 1, 1-11 (2005).

Truong, A.H.L. et al. "520 Poster A monoclonal antibody targeting Trop-2 exhibits anti-tumor efficacy in human cancer models as a monotherapy and demonstrates efficacy in combination therapy." European Journal of Cancer, Supplement, vol. 6, No. 12, p. 165, Oct. 24, 2008.

Truong, A.H.L. et al. "AR47A6.4.2, a naked monoclonal antibody targeting Trop-2, exhibits anti-tumor efficacy in multiple human cancer models as a monotherapeutic agent and demonstrates efficacy in combination therapy." Proceedings of the American Association for Cancer Research Annual Meeting, vol. 49, p. 948, Apr. 2008.

Truong, A.H.L. et al. "Functional antibodies targeting Trop-2 demonstrate in vivo efficacy in human pancreatic and other solid tumor xenograft models." Proceedings of the American Association for Cancer Research Annual Meeting, vol. 48, p. 217, Apr. 2007.

(Continued)

*Primary Examiner* — Sheela J Huff
(74) *Attorney, Agent, or Firm* — Steinfl & Bruno LLP

(57) ABSTRACT

The present invention teaches anti-Trop-2 monoclonal antibodies with high affinity and able to recognize different regions of the Trop-2 molecule, and uses thereof in the treatment and diagnosis of tumors, such as for example endometrium, breast, head and neck, colon-rectum, stomach, lung, ovary, prostate, pancreas, kidney, cervix and bladder (urothelial) tumors.

15 Claims, 7 Drawing Sheets

(56) References Cited

OTHER PUBLICATIONS

Figure 1:
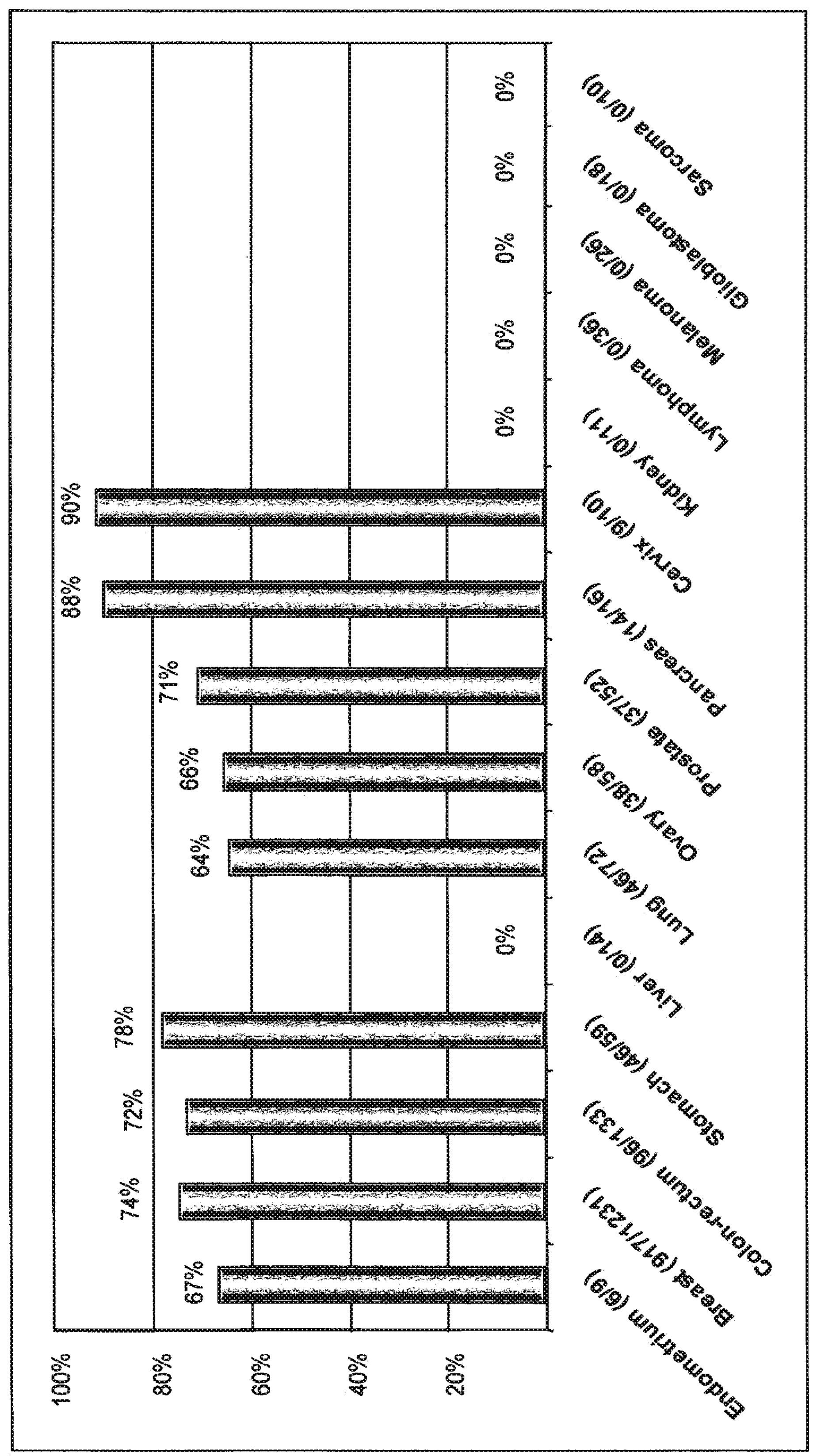

Ripani, E., et al. "Human Trop-2 is a tumor-associated calcium signal transducer." International Journal of Cancer, vol. 76, No. 5, pp. 671-676, Jan. 1, 1998.

Wang, J. et al. "Identification of Trop-2 as an oncogene and an attractive therapeutic target in colon cancers." Molecular Cancer Therapeutics, vol. 7, No. 2, pp. 280-285, Feb. 2008.

Written Opinion for PCT/IT2009/000035 filed on Feb. 5, 2009, in the name of Saverio Alberti.

International Search Report for PCT/IT2009/000035 filed on Feb. 5, 2009, in the name of Saverio Alberti.

1-Zhongde, W. et al. *Universal PCR amplification of mouse immunoglobulin gene variable regions: the design of degenerate primers and an assessment of the effect of DNA polymerase 3' to 5' exonuclease activity*. Journal of Immunological Methods, 2000, vol. 233, pp. 167-177.

| Targets | | %diff | %SEM | P |
|---|---|---|---|---|
| [illegible] | [illegible] | [illegible] | [illegible] | [illegible] |

| Targets | | %diff | %SEM | P |
|---|---|---|---|---|
| [illegible] | [illegible] | [illegible] | [illegible] | [illegible] |

a

| Targets | Specificity | %diff |
|---|---|---|
| Akt | absolute levels | 21.0 |
| Akt | S473 | no change |
| Bcl2 | absolute levels | -40.0 |
| CDK1 | Y15 | -46.4 |
| CREB | S133 | -67.4 |
| Csk | absolute levels | -43.9 |
| Cyclin D1 hmw | absolute levels | -43.5 |
| Cyclin D1 lmw | absolute levels | -96.9 |
| EGFR | absolute levels | no change |
| ERK1 | absolute levels | 54.1 |
| ERK1 | T202/Y204 | 13.4 |
| ERK2 | absolute levels | 29.9 |
| ERK2 | T202/Y204 | 56.9 |
| FAK | absolute levels | 55.4 |
| FAK | Y397 | 94.5 |
| GSK3α | S21 | -49.0 |
| GSK3α | Y279 | -32.2 |
| GSK3β | S9 | -33.7 |
| GSK3β | Y216 | -52.5 |
| JNK hmw | T183/Y185 | -53.7 |
| JNK lmw | T183/Y185 | -34.4 |
| Jun | absolute levels | 22.2 |
| Jun | S73 | -33.0 |
| MEK1/2 | S217/S221 | -30.6 |
| MEK3/6 | S189/S207 | -18.7 |
| MEK6 | S207 | -21.5 |
| MSK1/2 hmw | S375 | -24.0 |
| MSK1/2 lmw | S375 | -33.0 |
| NFkB p50 | absolute levels | 132.0 |
| p38 | absolute levels | 65.2 |
| p38 | T180/Y182 | -69.8 |
| p53 | S389 | -84.6 |
| PCNA | Pan-specific | -46.6 |
| PDK1 | S241 | -34 |
| PKCα | absolute levels | no change |
| PKCα | S657 | 71.5 |
| PTEN | absolute levels | -47 |
| Raf-1 | absolute levels | 66.4 |
| Raf-1 | S259 | 126.0 |
| Rb | absolute levels | -21.6 |
| Rb | S773 | -78.8 |
| S6K p70 hmw | T412 | -33.6 |
| S6K p70 lmw | T412 | -15.9 |
| Src | absolute levels | -18.2 |
| Src | Y534 | 17.8 |
| STAT1 | Y701 | -17.4 |
| STAT3 | S727 | -30.3 |

b

*Fig.3*

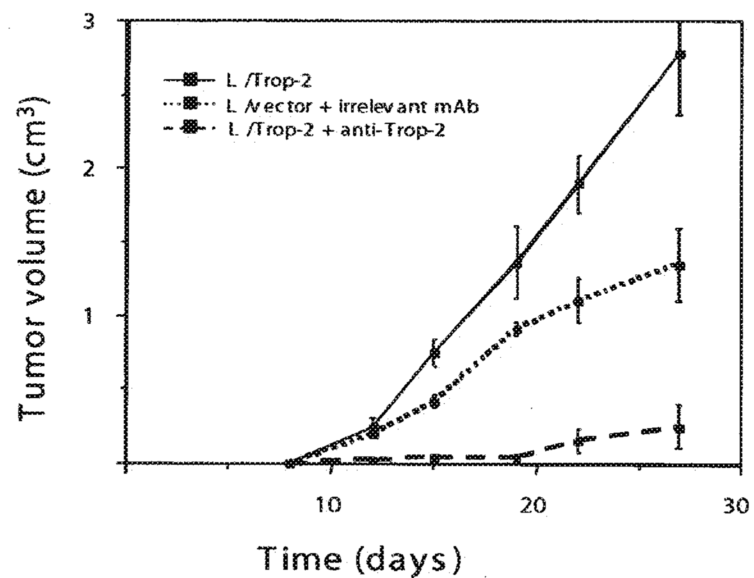
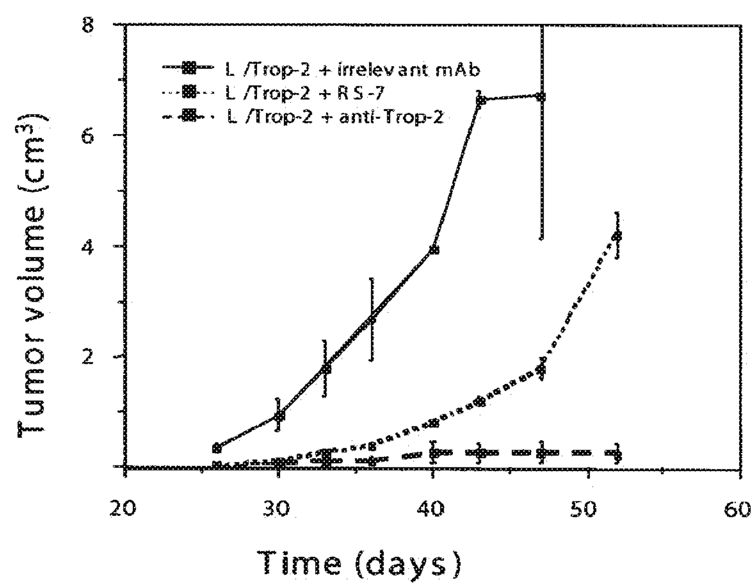
Fig.6

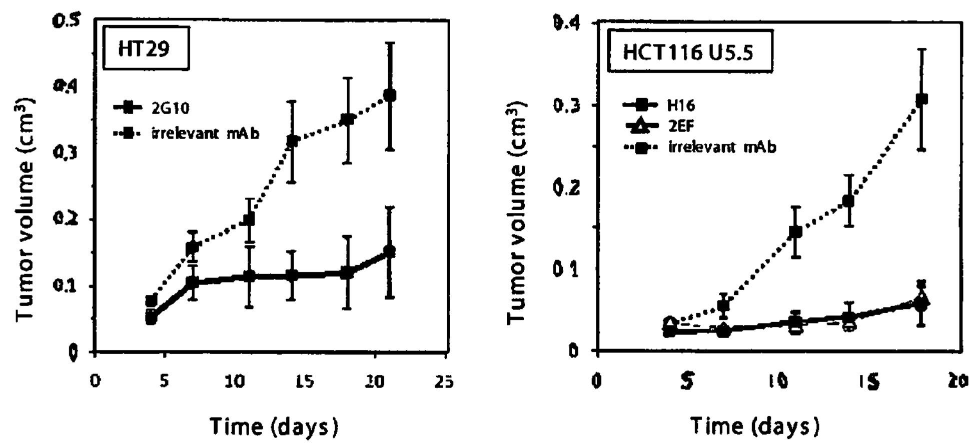
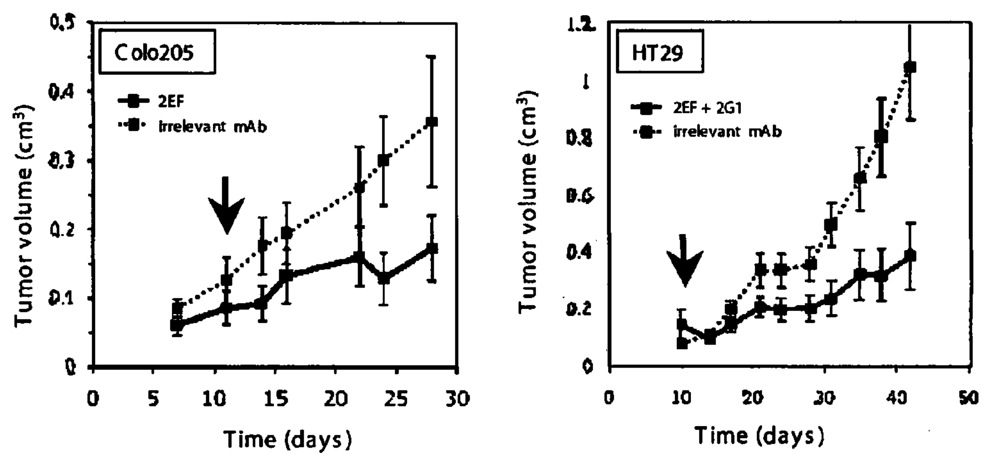
*Fig.7*

ANTI-TROP-2 MONOCLONAL ANTIBODIES AND USES THEREOF IN THE TREATMENT AND DIAGNOSIS OF TUMORS

CROSS REFERENCE TO RELATED APPLICATIONS

The present application is the US national stage of International Application PCT/IT2009/000035 filed on Feb. 5, 2009.

The present invention concerns anti-Trop-2 monoclonal antibodies and their uses in the treatment and diagnosis of tumors. More in particular the invention concerns anti-Trop-2 monoclonal antibodies having high affinity and able to recognize different regions of the Trop-2 molecule and their uses in the treatment and diagnosis of tumors such as for example endometrium, breast, head and neck, colon-rectum, stomach, lung, ovary, prostate, pancreas, cervix, kidney and bladder (urothelial) tumors.

Trop-2 (AC: P09758) is a molecule that transduces a signal that determines an increase in cytoplasmic calcium[1] and it is involved in cell-cell and cell/matrix adhesion in epithelial tissues. Trop-2 is also known as tumor-associated calcium signal transducer 2 (TACSTD-2)[2, 3], GA733-1, EGP, MR23, MR54, RS-7 e T16[4-6]. Trop-2 localizes all along the membrane in epithelial cells[4]. The extracellular domain of Trop-2, globular portion, contains an EGF-like domain, followed by a thyroglobulin domain and it is involved in cell adhesion. The globular region is followed by a region without cysteines, which is proposed to work as a supporting stem[3, 7]. The intracellular domain of Trop-2 is 26 aminoacid long and contains a HIKE domain[8], which includes a PKC phosphorylation site (Ser303)[9].

The Authors of the present invention have confirmed and extended previous data[4-6], showing that Trop-2 is expressed by the majority of tumors in man. DNA microarray, EST, SAGE, Northern blot e RT-PCR analyses showed TROP2 mRNA expression in ovarian, NSCLC, prostate, breast and colon cancer cell lines and in stomach, colon, breast, endometrium, kidney, lung and ovary human tumors. TROP2 mRNA expression was also detected in normal human breast tissue, in lung, uterus, prostate, salivary glands, pancreas, respiratory ducts, thymus, kidney and placenta.

An immunohistochemical analysis of Trop-2 protein expression performed on 1755 cases of human neoplasias (FIG. 1 and Table 1) showed that the Trop-2 protein is highly expressed in the vast majority of malignant epithelial neoplasias (between 64% and 90% of the cases). The highest prevalence of Trop-2 expression was found in cervix and pancreas tumors, followed by stomach, colon, breast and prostate cancers and by ovary, lung and endometrium neoplasias. Lymphomas, melanomas, brain tumors and sarcomas do not express Trop-2 (FIG. 1 and Table 1 concerning Trop-2 expression in human primary tumors and their corresponding metastases).

TABLE 1

| | Normal Tissues[a] | | | Tumors[b] | | Metastasi[c] | | |
|---|---|---|---|---|---|---|---|---|
| N of cases | High | Medium | Low or Absent | Higher | Lower | Higher | Lower | P[d] |
| Breast | 4 (4%) | 30 (30%) | 66 (66%) | 95 (95%) | 5 (5%) | 58 (58%) | 16 (16%) | <0.001 |
| Colon | 0 | 0 | 48 (100%) | 42 (88%) | 6 (12%) | 20 (42%) | 8 (17%) | 0.003 |

TABLE 1-continued

| | Normal Tissues[a] | | | Tumors[b] | | Metastasi[c] | | |
|---|---|---|---|---|---|---|---|---|
| N of cases | High | Medium | Low or Absent | Higher | Lower | Higher | Lower | P[d] |
| Stomach | 0 | 0 | 39 (100%) | 28 (72%) | 11 (28%) | 16 (41%) | 3 (9%) | 0.001 |
| Ovary | 0 | 0 | 10 (100%) | 9 (90%) | 1 (10%) | 6 (60%) | 2 (20%) | |

[a]expression in normal tissues.
[b,c]higher or lower expression in primary tumors with respect to normal tissues, and in metastases with respect to the corresponding primary tumors.
[d]P value from Wilcoxon test.

A direct function of Trop-2 in tumor development has been demonstrated both in vitro and in vivo. The introduction of Trop-2 in MTE 4-14 and Igrov-1 or its overexpression in KM12SM stimulated the growth of both fully transformed and simply immortalized cells (FIG. 2*a*), indicating that Trop-2 expression is both necessary and sufficient to stimulate the growth of tumor cells.

Similar results were obtained in experimental tumors (293 or L tumor cells injected subcutaneously in nude mice) (FIG. 2*b*). Trop-2 expression was shown to induce increased mitotic activity, nuclear pleomorphism and multinucleate giant cells. Tumor development was proportional to Trop-2 expression levels.

The deletion of Trop-2 cytoplasmic region abolished Trop-2-depended growth stimulation, showing that this region plays a key role in Trop-2 signaling (FIG. 2*b*). The tail contains a serine residue (S303) that is phosphorylated by PKC[9]. S303 mutagenesis abolished the growth stimulation activity, indicating that Trop-2 stimulatory activity is phosphorylation-dependent (FIG. 2*a*).

Proteomic and phosphoproteomic analyses on antibody microarrays have allowed the identification of downstream molecules involved in Trop-2 signaling (FIG. 3). Trop-2-induced expression alterations were shown for trans-membrane tyrosine-kinase receptors (PDGFR, Met, Ret, VEGFR), soluble tyrosine-kinases, serine/threonine-kinases, phosphatases, cell-cycle regulators and apoptosis regulatory molecules. Western blot analyses validated the antibody microrarray analyses for a reference set of molecules and phosphorylation sites. The results obtained indicate Trop-2-dependent activation of PKC-$\alpha$, FAK and Raf-1, involvement of the PTEN-Akt-GSK3$\alpha$/$\beta$-S6K pathway, modulation of ERK, JNK and p38 MAPK, induction of NF-$\kappa$B and modulation of apoptotic factors, p53 and Rb. The modulation of the key players of this model (e.g. ERK, Cyclin D1, NF$\kappa$B) was shown to be dependent on the presence of an intact Trop-2 cytoplasmic tail.

Metastatic spreading is the main cause of death in the majority of cancers in man[10]. Common tumors such as for example colon, breast and lung cancers in many cases have already generated metastases at the time of surgery. Metastatic tumors are often resistant to most of the currently available therapeutic attempts[10].

Therefore a better knowledge of the molecular mechanisms of tumor spreading could play a critical role for a better treatment of advanced neoplastic disease. In particular the identification of new markers of tumor aggressiveness and metastatic potential can contribute to the identification of the aggressive cases at an early stage and provide new targets for novel therapies[10].

Following this strategic approach the authors of the present invention showed that TROP2 is the only gene that is over-expressed in metastatic cells in different experimental systems. A large-scale analysis of Trop-2 expression in human primary cancers and their corresponding metastases revealed Trop-2 overexpression in the metastases from colon, stomach, breast and ovary tumors. This was confirmed by Northern and Western blot and by immunohistochemistry (FIG. 1 and Tables 1, 2).

Following this a causative role for Trop-2 in the spreading of metastatic cells was shown, transfecting the KM12SM colon tumor cell line with wild-type or mutagenized Trop-2. Transfected cells were then injected in the spleen of nude mice and metastatic potential was assessed. Trop-2 expression was shown to induce an increase in the metastatic spreading to the liver (in 90% of the cases). Table 2 shows the metastatic ability of the Trop-2-expressing cells.

TABLE 2

| KM12SM | % spleen take rate | size (cm$^3$) | % liver metastases | size (cm$^3$) |
|---|---|---|---|---|
| controls | 64.9 ± 8.7 | 0.11 ± 0.04 | 45.8 ± 14.8 | 0.50 ± 0.21 |
| wt Trop-2 | 69.0 ± 10.6 | 0.09 ± 0.03 | 90.0 ± 12.0[a] | 0.45 ± 0.18 |
| Dcyto Trop-2 | 100.0 ± 0[b] | 0.37 ± 0.23 | 76.9 ± 11.7 | 3.25 ± 0.64[c] |
| DHIKE Trop-2 | 84.6 ± 13.3 | 0.38 ± 0.22 | 63.6 ± 30.0 | 0.28 ± 0.15 |
| Trop-2 S303A | 90.0 ± 8.3 | 0.28 ± 0.21 | 88.9 ± 6.7 | 0.85 ± 0.55 |
| Trop-2 E→K | 66.7 ± 17.6 | 0.20 ± 0.12 | 75.0 ± 33.3 | 2.20 ± 0.95[d] |

[a]Fisher exact test: P = 0.0114 versus controls.
[b]Fisher exact test: P = 0.0382 versus wt Trop-2.
[c]Student T test: P < 0.0001 versus wt Trop-2.
[d]Student T test: P = 0.0204 versus wt Trop-2.

Trop-2 expression also modified growth patterns, apoptosis induction, cell morphology, cell-replication rate and metastasis dimensions.

The high frequence and expression levels of Trop-2 in human tumors and in their corresponding metastases have made this molecule an attractive target for "adoptive" immunotherapy, i.e. based on the administration of experimentally-produced antibodies (FIG. 1 and Table 1).

Other monoclonal antibodies directed against Trop-2 have been previously generated[4-6], but they have not essentially been utilized in clinical trials as anti-tumor drugs.

Moreover many antibodies have low affinity, while it is known that high affinity antibodies targeted against a molecule that is structurally analogous to Trop-2 (Trop-1, Ep-CAM, GA733-2)[3, 7] can be more cytotoxic towards tumor cells. In vitro data on the effect of an antibody affinity and of the density of the target antigen on antibody-dependent cellular cytotoxicity (ADCC) efficiency revealed that the high affinity of an antibody can induce the killing of cells with low levels of expression of the antigen, or, if with comparable levels, with higher efficacy[11]. Since heterogeneity of expression of the target antigen is a common feature in human tumors, the use of high affinity antibodies could play an important role in achieving better clinical results.

Moreover most of the anti-Trop-2 monoclonal antibodies at present available on the market, e.g. T16, have been generated using myeloma cell lines such as NS-1 or SP2-1 as fusion partners, which retains the expression of the parental immunoglobulin light chain. This caused these antibodies to be actually heterogeneous mixtures of antibodies with one, both or neither light chain directly participating in Trop-2 recognition.

The patent submissions WO03/074566, US2004/001825, US2007/212350 and US2008/131363 are known, theaching RS7 antibodies and their uses in the treatment and diagnosis of tumors.

The RS7 monoclonal antibody was obtained through the immunization of mice with tissue from lung squamous carcinoma, i.e. without selecting for reactivity against specific and different portions of the Trop-2 molecule. This prevents the synergic and personalized utilization of the various monoclonal antibodies, i.e. the use of the best monoclonal antibody for each individual tumor, as determined by the post-translational modifications of Trop-2 and by the ability of this molecule to generate intracellular signals that control tumor growth.

The patent submission WO2008/144891 is known, which teaches an anti Trop-2 monoclonal antibody for the treatment of tumors. Nevertheless the AR47A6.4.2 monoclonal antibody there described derives from the selection of antibodies with cytotoxic or cytostatic in vitro capabilities. In other terms this selection is not based on the in vivo efficacy, which is the fundamental parameter by which the efficacy of these antibodies should be evaluated. In fact the above mentioned submission does not disclose any proof of improvement with respect to prior art antibodies such as RS7 through a comparison of efficacies.

Moreover the AR47A6.4.2 monoclonal antibody showed efficacy against a single type of tumor (BxPC-3) at an advanced stage of growth, already growing in the experimental animal, which is considered to be the most stringent and reliable test of the activity on experimental tumors.

The AR47A6.4.2 monoclonal antibody was obtained by the immunization of mice with tissue from an ovarian tumor, i.e. without selecting for reactivity against specific and different portions of the Trop-2 molecule. As in the case of the RS7 antibody this prevents the synergic and personalized use of the different monoclonal antibodies, i.e. using the best monoclonal antibody for each individual tumor, as determined by the post-translational modifications of Trop-2 and by the ability of this molecule to generate intracellular signals that control tumor growth.

Finally the patent submission WO2008/144891 uses the mouse as only experimental model to show the lack of toxicity of the AR47A6.4.2 monoclonal antibody. The mouse does not express human Trop-2, therefore is inadequate for verifying the toxicity of anti-Trop-2 antibodies against normal cells. On the contrary in the present submission teaches the expression of Trop-2 in epithelial cells from epidermidis, esophagus, exocrine pancreas, urothelium and other tissues in man. This implies a potentially severe expected cytotoxicity, for example as acute pancreatitis, in the case of systemic administration (e.g intravenous), as shown for anti-Trop-1 antibodies (ING-1).

Therefore in the light of what has been described above there is clearly the need for new anti-Trop-2 monoclonal antibodies able to overcome the disadvantages of the prior art antibodies.

In particular it is important that anti-tumor monoclonal antibodies (es. targeted against Her2/neu) are directed against specific portions of the molecule, so as to avoid specific conformational changes or interactions with other signaling molecules, which play a fundamental role in determining the antitumor therapeutic efficacy[12].

Another important aspect is the possibility to have multiple antibodies, which do not compete for the binding to Trop-2. This makes it possible to bind higher numbers of tumor cells, when the targets of the individual antibodies (epitopes in technical terms) are selectively expressed at different development or differentiation stages of the tumor. Moreover this allows for the simultaneous binding of a higher number of antibody molecules to their target, with a corresponding increase in efficacy.

The authors of the present invention have now prepared new anti-Trop-2 monoclonal antibodies which are homogeneous and with high affinity and which are targeted against different regions of the molecule (FIGS. 4 and 5), at variance with the antibodies already known, for an efficient utilization in biomedical applications. The anti-Trop-2 antibodies taught by the present invention are active against the growth of multiple types of tumors such as for example Colo-205, HCT-116 and HT29 colon cancers; SKOV ovarian cancer; SKBR3 and MDA MB468 breast cancer. Moreover the antibodies taught by the present invention have a higher anti-tumor activity with respect to prior art RS7 antibodies, as shown in experimental models of human tumors injected in immuno-depressed mice (FIG. 6).

The authors of the present invention have developed novel strategies for the generation of monoclonal antibodies able to recognize different regions of the Trop-2 molecule. For the generation of new hybridoma cell lines secreting monoclonal antibodies directed against Trop-2, Balb/c mice were subjected to multiple immunization cycles utilizing the entire extracellular portion of the human Trop-2 molecule (NCBI RefSeq NM__002353)[3], produced by mammalian cell lines (L and 293) or by baculoviruses expressing the corresponding constructs.

A pivotal point of the anti-Trop-2 hybridoma isolation strategy was the selection procedure of the hybridoma cell populations for their specific reactivity against TROP2-transfected L cells and absence of reactivity against empy-vector control L transfectants, which made the screening procedure both stringent and effective. This screening procedure was performed by cytofluorimetry or ELISA tests on transfected or non transfected L cells.

The procedures employed in the present invention make use of ELISA and similar assays on recombinant Trop-2 proteins or portions of the protein, produced in insect cells infected with Trop-2-baculovirus or in mammalian cells. This allowed the utilization of recombinant Trop-2 proteins with native folding and glycosylation, therefore stringently corresponding to the molecules actually expressed by the tumor cells, for an efficient screening.

Moreover, the authors generated vectors expressing only the globular or the stem region of Trop-2. This allowed the specific selection of monoclonal antibodies targeted against either portion of the molecule (FIG. 4) and therefore potentially provided with differential or interfering capabilities towards omotypic aggregation/cell adhesion or penetration through already established Trop-2 molecular networks, respectively.

Figure 5:
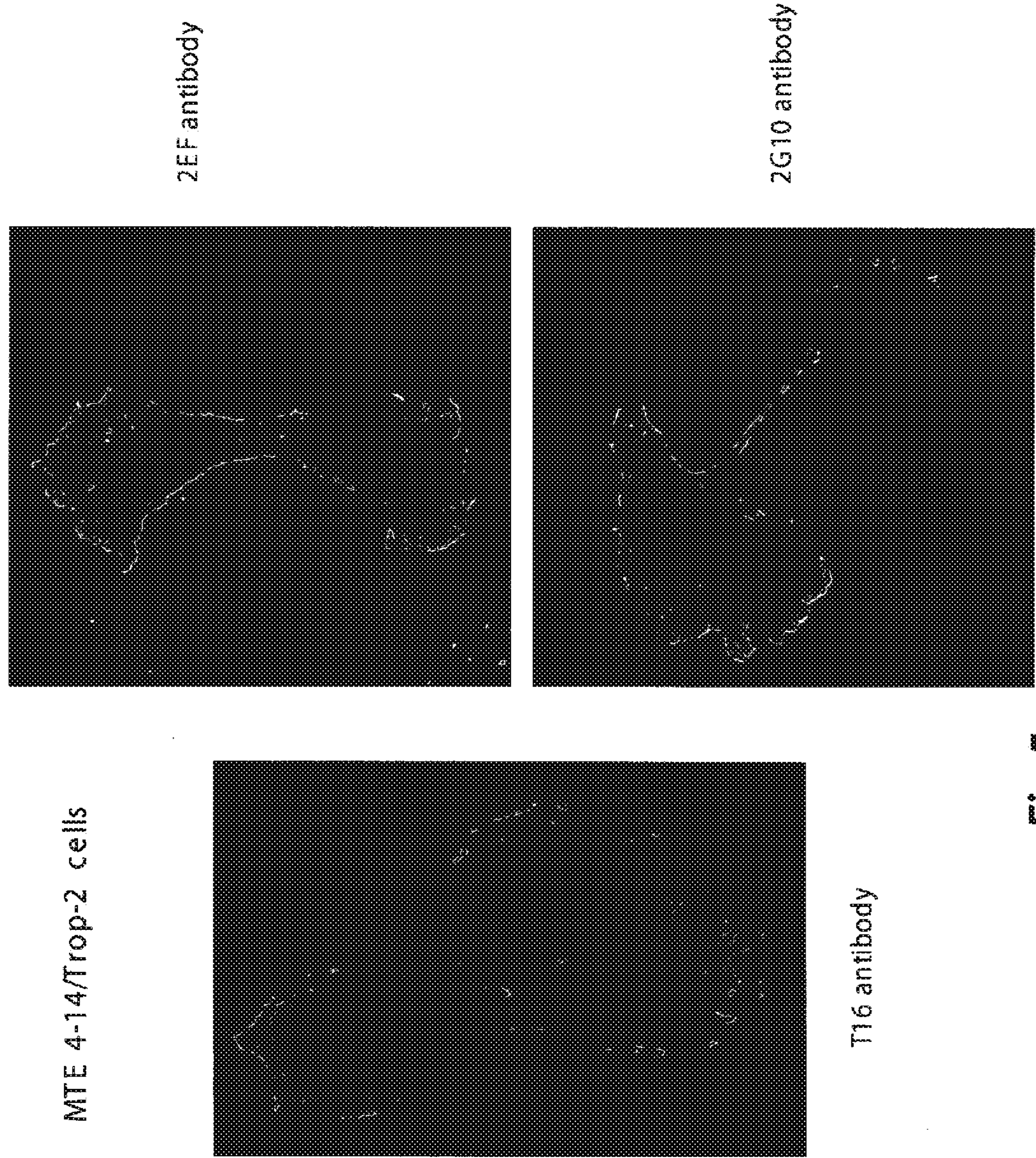

Formal proof of the recognition of the Trop-2 molecule by the monoclonal antibodies generated as described above is constituted by the ability of these antibodies to stain the murine cell line MTE-4-14 transfected with the human Trop-2 gene, as seen in immunofluorescence experiments (FIG. 5).

These new technologies allowed to obtain anti-Trop-2 monoclonal antibodies with high affinity for the wild-type molecule and specificity for different portions of the molecule. clonal antibodies. The efficacy of the monoclonal antibodies targeted against Trop-2 was shown in nude mice using as models either fibrosarcomas originated by L cells expressing Trop-2 or xenografts of human tumor cell lines, e.g. from ovary, breast and colon tumors. The monoclonal antibodies were then selected that proved to be the best/most effective in vivo[4], reaching essentially the complete inhibition of tumor growth (FIGS. 6 and 7).

As outlined above, the antibodies taught by the present invention showed a higher efficacy with respect to the RS7 antibody (FIG. 6). The antibody used in these experiments is the mRS7 monoclonal antibody, as taught in the patent submission WO03/074566, and shown in this same submission to have the same affinity and binding activity as the cRS7 ed hRS7 variants.

As far as the utilization strategies of anti-Trop-2 antibodies are concerned, it was also found that the potential systemic toxic effects, connected with the therapeutic use of high affinity anti-Trop-2 antibodies, could be reduced by optimization strategies which would include "chasing" procedures to eliminate the residual circulating antibody quickly and in a safe/reproducible way. Complementary to this approach, the use of high affinity anti-Trop-2 antibodies can be applied to locoregional treatments. In particular, the authors of the present invention have found that the monoclonal antibodies thus prepared can be advantageously employed in therapeutic IP administration, where, at variance with systemic diffusion, the 'chasing' of the antibody is operated by the adsorption to the tumor cells through specific bonds. This is due to the combination of the expected pharmacokinetics following intraperitoneal antibody administration and of the high levels of expression of Trop-2 by ovarian carcinoma and its metastases (FIG. 1 and Table 1). A second strategy based on essentially corresponding principles is the intra hepatic artery administration in the case of hepatic metastases of colon carcinoma. These approaches should be understood as extended to include similar cases, e.g. local administration in head and neck tumors, as well as intrapleural, intravescical, and in general intralesional administration.

Therefore it is a specific embodiment of the present invention a combination comprising or consisting of at least two isolated anti-Trop-2 monoclonal antibodies chosen in the group of the anti-Trop-2 monoclonal antibodies produced by the hybridoma cell lines deposited at the AID-ICLC in Genoa (Italy) on Aug. 27, 2008 with the deposit number PD 08019, PD 08020 or PD 08021.

Preferably the combination includes or consists of the anti-Trop-2 monoclonal antibodies produced by the hybridoma cell lines having deposit numbers PD 08019, PD 08020 and PD 08021, or PD 08019 and PD 08020, or PD 08019 and PD 08021, or PD 08020 and PD 08021.

Further embodiments of the present invention are each anti-Trop-2 monoclonal antibody produced by the hybridoma cell line having deposit number PD 08019, PD 08020 or PD 08021.

The antibodies taught by the present invention can be fully humanized or chimeric antibodies, where the murine constant region is substituted by human constant regions[13], or variants containing at least one of the CDRs of the variable region of the corresponding light and/or heavy chains, possibly mutagenized to modify their affinity for the target.

Figure 4:
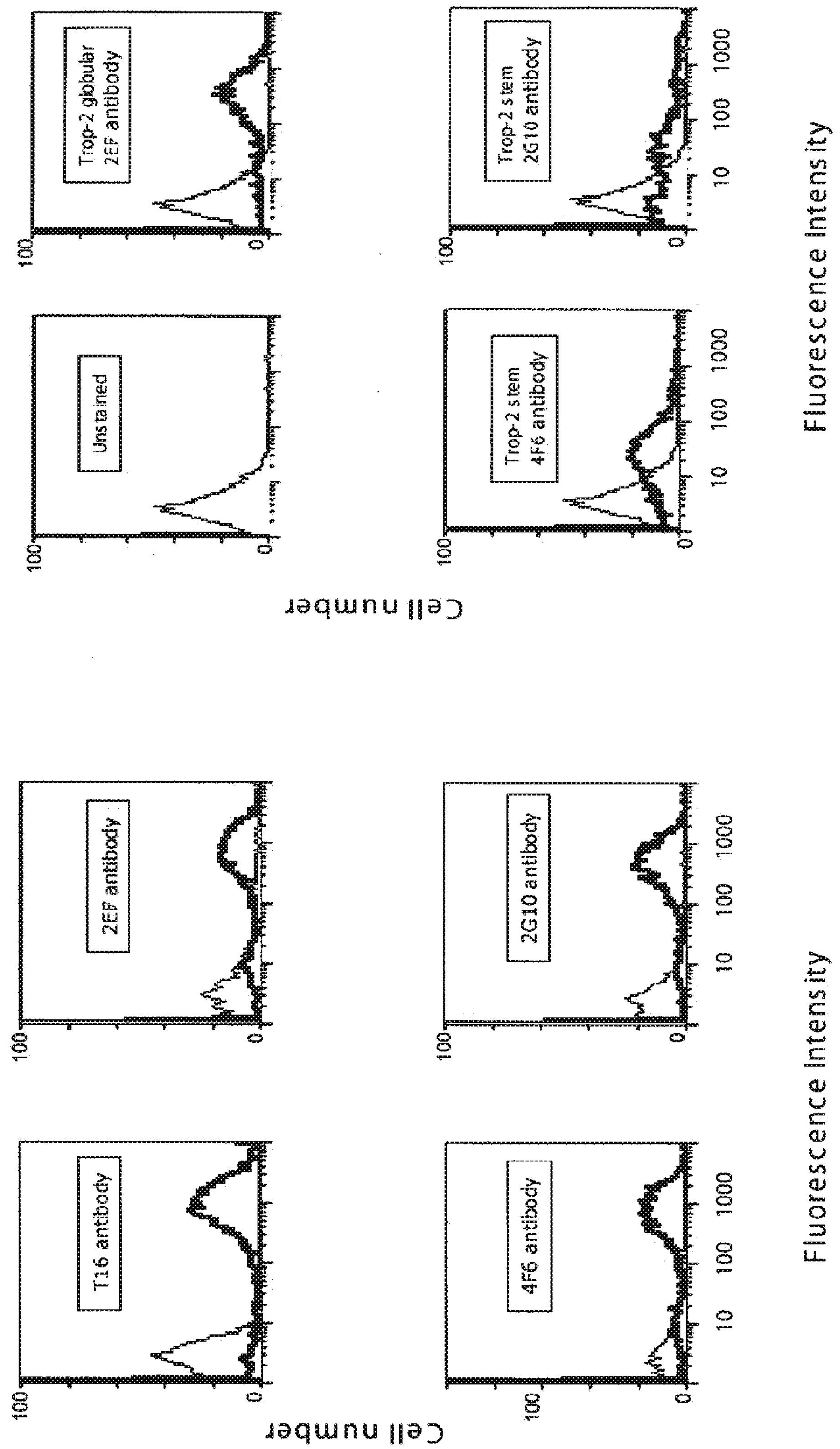

The epitopes recognized by the above described antibodies are localized in the globular region or in the stem (FIG. 4).

Further to the above mentioned antibodies, antibody or chimeric molecule fragments, Fv, Fab, F(ab)2 fragments, single chain or multimeric anti-Trop-2 antibodies could be utilized. Antibodies, fragments or antibody chimeras can come from, or be engineered in, IgM, IgD, IgG, IgA, or IgE isotypes.

Moreover, recombinant derivatives of the antibodies taught by the present invention can be prepared, where the constant region is substituted by, or conjugated with, a biologically active partner, e.g. avidin or its derivatives, or growth factor, toxins, cytokines, anti-tumor drugs and radioisotopes or any other compound that is biologically active and/or useful to increase the anti-tumor therapeutic efficacy.

The nucleic acids coding for the above described proteins can be cloned in an expression vector. An expression vector is intended as a plasmid, cosmid, pahgemid, BAC, baculovirus, vectors for yeasts or plants, phage vectors, Ti or similar plasmids, including the vectors for transgenic organisms, knock-out and for gene therapy. Therefore cells that contain and possibly express nucleic acid molecules as taught by the present invention can be prepared.

Moreover the present invention teaches a pharmaceutical composition comprising or consisting in, as active ingredient, a combination as defined above or an anti-Trop-2 monoclonal antibody as defined above, in association with one or more excipients and/or adjuvants that are pharmaceutically acceptable. In particular, the pharmaceutical composition can be in a form acceptable for intraperitoneal, intrapleural, intravesical, intralesional administration or administration through the hepatic artery.

A further embodiment of the present invention is the use of the combinations as defined above or the anti-Trop-2 monoclonal antibody as defined above or the composition as defined above for the preparation of a medicament for the prevention or the cure of tumors and/or metastases.

The tumor, for example expressing Trop-2, can be treated before or after its removal, by means of the administration of antineoplastic agents such as the antibody or its derivatives, alone or in combination with other therapeutic modalities. In particular the administration modalities of the anti-Trop-2 antibodies and their derivatives can be either systemic or locoregional, e.g. intraperitoneal, intrapleural, intravesical, intra-hepatic artery or intralesional (intratumor). An indicative and not exhaustive list of targets for therapies based on anti-Trop-2 antibodies includes endometrium, breast, head and neck, colon-rectum, stomach, lung, ovary, prostate, pancreas, cervix, kidney and bladder (urothelial) tumors.

Moreover the present invention teaches the use of the combinations as defined above, of an anti-Trop-2 monoclonal antibody as defined above, for the diagnosis of tumors in vitro.

A further embodiment of the present invention is a kit for the diagnosis of tumors in vitro comprising or consisting in the combinations as defined above, or the anti-Trop-2 monoclonal antibody as defined above or the composition as defined above.

The antibodies taught by the present invention or their derivatives can be fused to sequences, single residues or synthetic molecules (tags) that allow antibody purification by affinity cromatography. The tags utilized can be used as detection molecules or indicators (e.g. radioisotopic or fluorescent tags) or enzymatic tags able to catalyze a detectable substrate modification, both for diagnostic use in the lab and for imaging. The diagnostic techniques that can be utilized are for example optical, confocal, multiple foton and electronic microscopy, ELISA, Western blotting, immunoprecipitation, radioimmunological techniques and similar others.

The antibodies taught by the present invention can be used for the preparation of compositions for the detection of Trop-2 expressing neoplasias, including in vivo tumor imaging. Anti-Trop-2 antibodies can be linked to radioactive isotopes or fluorescent tracers, e.g. quantum dots or organic chromophores or enzymes which can be detected by chemiluminescence. The signal originated by labeled anti-Trop-2 antibodies is detectable by scanners or tomography instrumentation, according to the principles of currently used advanced equipment such as TAG/PET.

The present invention will be now described by way of illustration and example, according, but not limited, to, some of its preferred embodiments, with particular reference to the figures of the enclosed drawings.

FIG. 1: Trop-2 protein expression in human tumors.

Percentages of Trop-2 expression in human tumors are indicated at the top of the panel. The absolute numbers of samples analyzed are indicated at the bottom of the panel.

Figure 2:
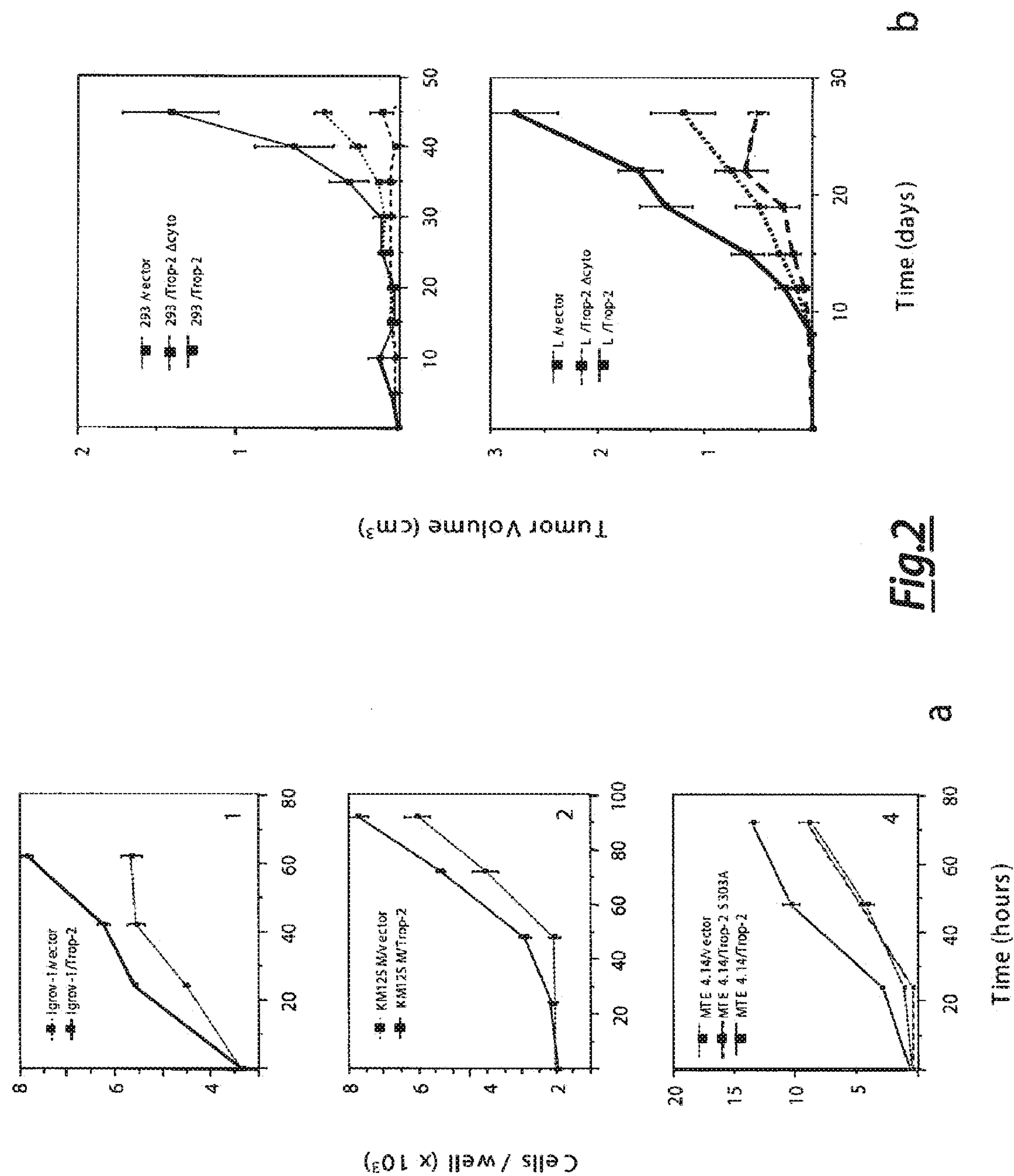

FIG. 2: Cell growth induction by Trop-2.

(a) In vitro growth rates of Igrov-1, KM12SM and MTE 4-14 cells transfected with wild-type Trop-2 or Trop-2 which is deleted in the cytoplasmic tail (Δcyto) or mutated in the PKC phosphorylation site (S303A). Control cells correspond to dotted lines; wt Trop-2 transfectants correspond to solid lines; mutagenized Trop-2 transfectants correspond to dashed lines. Bars: standard errors of the means of the measurements.

(b) In vivo growth rates of tumors from L (fibrosarcomas) and 293 (carcinomas) cells. Cells transfected with vector alone correspond to dotted lines; wt Trop-2 transfectants correspond to solid lines; mutagenized Trop-2 transfectants correspond to dashed lines.

FIG. 3: Proteomic analysis of Trop-2 signaling pathways (a) MTE 4-14 cells stably transfected with Trop-2 or control vector were analysed on antibody arrays for the expression levels of various signaling molecules. The table shows the significant changes in the protein absolute levels (pan) or in phosphorylation levels of specific sites. Grey: percentage increases (left) or decreases (right) in cells transfected with Trop-2 with respect to the controls. P: T-test analysis of Trop-2 expression levels with respect to the controls.

(b) Parallel Western blot analyses.

FIG. 4: Specific recognition of Trop-2 by the monoclonal antibodies produced—flow cytometry analysis.

(a) Murine fibrosarcoma L cells (thin lines) or L cells transfected with wt Trop-2 (thick lines) were incubated with anti-Trop-2 monoclonal antibodies. T16 was utilized as a positive control antibody.

(b) Murine fibrosarcoma L cells (thin lines) or L cells transfected with Trop-2 deletion mutants corresponding to the globular or the stem regions, respectively (thick lines), were incubated with anti-Trop-2 monoclonal antibodies. Antibody binding was detected with a goat-anti-mouse antiserum conjugated with the Alexa488 fluorophor.

FIG. 5: Specific recognition of Trop-2 by the monoclonal antibodies produced—confocal microscopy analysis.

The murine thymic epithelial cells MTE 4-14 transfected with the human TROP2 gene were incubated with the indicated Trop-2 monoclonal antibodies. Antibody binding was detected with a goat-anti-mouse antiserum conjugated with the Alexa488 fluorophor. T16 was utilized as a positive control antibody.

FIG. 6: Inhibition of the growth of tumors treated with the indicated anti-Trop-2 antibodies.

(a) Cells transfected with vector alone and treated with an antibody with irrelevant specificity (anti-dansyl) correspond to dotted lines; TROP2 transfectants correspond to solid lines; TROP2 transfectants treated with anti-Trop-2 antibodies correspond to dashed lines. Bars: standard errors of the means of the measurements.

(b) Efficiency of growth inhibition of tumors treated with different anti-Trop-2 antibodies. TROP2 transfectants treated with an antibody with irrelevant specificity (anti-dansyl) correspond to solid lines; TROP2 transfectants treated with RS7 anti-Trop-2 antibodies correspond to dotted lines; TROP2 transfectants treated with the anti-Trop-2 antibodies here described in this application correspond to dashed lines. Bars: standard errors of the means of the measurements.

FIG. 7: Inhibition of the growth of advanced, already growing tumors treated with the indicated anti-Trop-2 antibodies, compared with tumors treated in a prophylactic manner.

(a) Efficiency of growth inhibition of tumors (HT29 e HCT-116 U5.5) treated with different anti-Trop-2 antibodies in a prophylactic manner (co-injection of tumor cells and of antibodies). Tumors treated with an antibody with irrelevant specificity (anti-dansyl) correspond to dotted lines; tumors treated with different anti-Trop-2 antibodies (2G10: squares, 2E7: triangles) correspond to solid lines. Bars: standard errors of the means of the measurements.

(b) Efficiency of growth inhibition of tumors (COLO205 e HT29) treated with different anti-Trop-2 antibodies at an advanced stage. Tumors treated with an antibody with irrelevant specificity (anti-dansyl) correspond to dotted lines; tumors treated with different anti-Trop-2 antibodies (2E7 and 2G10) correspond to solid lines. In the right panel are shown the results of a combined treatment with 2E7 and 2G10. Vertical arrows indicate the beginning of the treatment with antibodies. Bars: standard errors of the means of the measurements.

EXAMPLE 1

Preparation and Efficacy Study of the Efficacy of the Monoclonal Antibodies as Taught by the Present Invention Flow Cytometry The binding of the anti-Trop-2 monoclonal antibodies to the surface of tumor and transfected cells was analysed by flow cytometry on cell lines (FIG. 4). Staining and analysis were performed essentially as described[15].

Generazione Degli Anticorpi Monoclonali

Balb/c mice were subjected to multiple immunization cycles utilizing the entire extracellular region of the human Trop-2 molecule (nt 339-1157 of NCBI RefSeq NM_002353)[3], produced by mammalian cell lines (L and 293) or by baculoviruses containing and expressing the corresponding constructs The constructs were prepared by PCR amplification of the TROP2 gene with the following primers:

```
hT2-sigpeptide_EcoRI-for          (SEQ ID NO: 1)
5' CCCCGAATTCATGGCTCGGGGCCCCGGCCTCGC

hT2-6his-XbaI-rev                 (SEQ ID NO: 2)
5' CCCCCTCTAGATCACGTGATGGTGATGGTGATG

CCCCCCGGTGAGGCGCTTCATGGAG
```

A 6-histidine tag was added to the C-terminus to allow for an easier purification of the protein. The PCR band was subcloned into the vector pBJI-neo for expression in mammalian cells or pFastBac HTA for expression in baculovirus (“Bac to Bac” Baculovirus expression system, Invitrogen, USA). The recombinant Trop-2 protein that was produced in this way was subsequently purified from the culture medium by means of affinity cromatography on Ni-NTA Agarose (Qiagen, The Netherlands). Splenocytes from immunized mice were fused to myeloma Sp2/0 or NS-0 cells, following methodologies known in the art[14]. Hybridoma cells were selected for specific reactivity against L cells transfected with TROP2 and for absence of reactivity against L cells transfected with the empy vector. These assays were integrated with ELISA tests on recombinant Trop-2 proteins or on portions of them. In particular various expression vectors were generated for mammalian cells and baculovirus expressing either the globular region alone (nt 339-773) or the stem region alone (nt 774-1157) of the extracellular region of Trop-2, with the aim of selecting monoclonal antibodies specifically targeted against either region (FIG. 4). The constructs were prepared by PCR amplification of the TROP2 gene with the following primers:

```
hT2-gl_EcoRI -for
                                        (SEQ ID NO: 3)
5' CCCCGAATTCTAAATGGCTCGGGGCCCCGGCCTCGC

hT2-gl_HindIII -rev
                                        (SEQ ID NO: 4)
5'

GCGAAGCTTTTAGTGATGGTGATGGTGATGGCAGCGTAGGCTCAGGT

C

for the globular region;
hT2-st_EcoRI -for
                                        (SEQ ID NO: 5)
5'CCCCGAATTCTAAATGGCTCGGGGCCCCGGCCTCGCGC

CGCCACCGCTGCGGCTGCCGCTGCTGCTGCTGGTGCTGGCGGCGG

ATGAGCTGGTGCGCACC

hT2-st_HindIII -rev
                                        (SEQ ID NO: 6)
5'GCGAAGCTTCTAGTGATGGTGATGGTGATGCCCCCCGGT
GAGGCGCTTCATGGAG
```

for the stem region. In both cases a 6-histidine tag was added to the C-terminus to allow for an easier purification of the recombinant proteins.

Subsequently the fragments were cloned in the pYFP-AFP vector for expression in mammalian cells or pFastBac HTA for expression in baculovirus.

SDS-PAGE and Western Blotting Analyses

Antibody preparations or lysates from target tissues were run on SDS-PAGE gels, then stained with Comassie blue (Invitrogen, USA). For Western blot analyses gels were electro-transferred onto nitrocellulose membranes. Membranes were incubated with primary and secondary antibodies to detect target molecules by chemiluminescence.

Cell Transfection

Transfections with constructs coding for Trop 2 were performed either as described in[15] or by lipofection (Gibco-BRL, USA).

Confocal Microscopy

Samples were stained with anti-Trop-2 monoclonal antibodies conjugated to Alexafluor-488, or with the same unconjugated antibodies revealed by a goat anti-mouse antiserum conjugated to Alexafluor-488. After fixation in 4% paraformaldheyde in PBS for 30 minutes at room temperature and permeabilization in PBS 10% serum and 0.05% saponin, cells were incubated with the antibodies for 30 minutes at room temperature, followed if necessary by a second incubation with the goat anti-mouse antiserum. Slides were then washed and mounted for observation.

Immunohistochemistry

Sections of normal and tumor tissues were analyses by immunohistochemistry essentially as described[16].

In Vivo Models: Xenografts in Athymic Nude Mice

L or 293 cell lines, transfected with TROP2 or with the control empty vector, or human carcinoma (breast, ovary, colon) cells natively expressing or transfected with Trop-2 were subcutaneously injected in groups of nude mice (10 animals/group). For the coinjection protocol (prophylactic treatment), on the day of the injection the mice were treated IP with 200 μg of anti-Trop-2 or irrelevant monoclonal antibodies. For the treatment of established tumors, already grown in the injected animals, the nude mice were treated with 800 μg of anti-Trop-2 or irrelevant monoclonal antibodies, starting the treatment at a tumor volume of about 0.1 $cm^3$. Three more doses were administered at day 7, 15 and 22 from the beginning of the treatment, as indicated. In all the groups tumor growth was measured twice a week essentially as indicated[17].

Sequencing of the Variable Regions of the Anti-Trop-2 Monoclonal Antibodies.

RNA was extracted from the hybridomas producing the anti-Trop-2 monoclonal antibodies taught by the present invention using Trizol (Invitrogen, USA). The variable regions of both the heavy (VH) and light (LH) chain of the immunoglobulin genes were amplified from total RNA by RT-PCR as described[18]. Amplified fragments were sequenced using the BigDye Terminator v3.1 Cycle Sequencing Kit (Applied Biosystems, USA); the reaction products were analyses on an Applied Biosystems 3130xl Genetic Analyzer. The FR and CDR regions of the VH and VL were identified according to the ImmunoGenetics Information System (IMGT) as described[19].

The coding regions (open reading frame, ORF) and aminoacid sequences corresponding to the VH and VL of each anti-Trop-2 monoclonal antibody are listed below:

VH of the 4F6 Monoclonal Antibody (Hybridoma Cell Line N. PD 08019)

ORF (SEQ ID NO: 7)

```
1     CAGCTGCAGC AGTCTGGAGC TGAGGTGGTG
      AAGCGTGGGG CTTCAGTGAA GCTGTCCTGC AAGACTTCTG
      GCTTCACCTT CAGCAGTAGC TATATAAGTT

101   GGTTGAAGCA GAAGCCTCGA CAGAGTCTTG
      AGTGGATTGC ATGGATTTAT GCTGGAACTG GTGGTACTAG
      CTATAATCAG AAGTTCACAG GCAAGGCCCA

201   ACTGACTGTA GACACATCCT CCAGCACAGC
      CTACATGCAA CTCAGCAGCC TGACATCTGA GGACTCTGCC
      ATCTATTACT GTGCAAGACA TAACCCTTGT

301   TACTATGCTA TGGATTACTG GGGTCAAGGA
```

FR1: 1-69
CDR1: 70-93
FR2: 94-144
CDR2: 145-168
FR3: 169-282
CDR3: 283-330

Aminoacid sequence (SEQ ID NO: 8)

```
1     DVQLEQFGAE LVRPGTSVKM SCKAAGYTFT NYWIGWVKQR
      PGHGLEWIGD IYPGGGYTNY NEKFKGKATL TADTSSSTAY
      MQLSSLTFED FAIYYCARGT

101   GGGDYWGQG
```

FR1: 1-25
CDR1: 26-33
FR2: 34-50
CDR2: 51-58
FR3: 59-96
CDR3: 97-110

VL of the 4F6 Monoclonal Antibody (Hybridoma Cell Line N. PD 08019)

ORF (SEQ ID NO: 9)

```
1     TATTGTGATC ACCCAGTCTC CAGCATCCCT
      GTCCATGGCT ATAGGAGAAA AAGTCTCCAT CAGATGCATA
      ACCAGCACTG ATATTGATGA TGATATGAAC

101   TGGTACCAGC AGAAGCCAGG GGAACCTCCT
      AAGCTCCTTA TTTCAGAAGG CAATACTCTT CGTCCTGGAG
      TCCCATCCCG ATTCTCCAGC AGTGGCTATG

201   GTACAGATTT TGTTTTTACA ATTGAAAACA
      TGCTCTCAGA AGATGTTGCA GATTACTACT GTTTGCAAAG
      TGATAACTTG CCGTACACGT TCGGAGGGGG

301 A
```

FR1: 1-76
CDR1: 77-94
FR2: 95-145
CDR2: 146 154
FR3: 155-261
CDR3: 262-301

Aminoacid sequence (SEQ ID NO: 10)

```
1     IVITQSPASL SMAIGEKVSI RCITSTDIDD DMNWYQQKPG
      EPPKLLISEG NTLRPGVPSR FSSSGYGTDF VFTIENMLSE
      DVADYYCLQS DNL
```

FR1: 1-25
CDR1: 26-31
FR2: 32-48
CDR2: 48-51
FR3: 52-87
CDR3: 88-93

VH of the 2G10 Monoclonal Antibody (Hybridoma Cell Line N. PD 08020)

ORF (SEQ ID NO: 11)

```
1     CAGCTGCAGC AGTCTGGAGC TGAGGTGGTG
      AAGCGTGGGG CTTCAGTGAA GCTGTCCTGC AAGACTTCTG
      GCTTCACCTT CAGCAGTAGC TATATAAGTT

101   GGTTGAAGCA GAAGCCTCGA CAGAGTCTTG
      AGTGGATTGC ATGGATTTAT GCTGGAACTG GTGGTACTAG
      CTATAATCAG AAGTTCACAG GCAAGGCCCA

201   ACTGACTGTA GACACATCCT CCAGCACAGC
      CTACATGCAA CTCAGCAGCC TGACATCTGA GGACTCTGCC
      ATCTATTACT GTGCAAGACA TAACCCTTGT

301   TACTATGCTA TGGATTACTG GGGTCAAGGA
```

FR1: 1-69
CDR1: 70-93
FR2: 84-144
CDR2: 145-168
FR3: 169-282
CDR3: 283-330

Aminoacid sequence (SEQ ID NO: 12)

```
1     DVQLEQFGAE LVRPGTSVKM SCKAAGYTFT NYWIGWVKQR
      PGHGLEWIGD IYPGGGYTNY NEKFKGKATL TADTSSSTAY
      MQLSSLTFED FAIYYCARGT

101   GGGDYWGQG
```

FR1: 1-25
CDR1: 26-33
FR2: 34-50
CDR2: 51-58
FR3: 59-96
CDR3: 97-110

VL of the 2G10 Monoclonal Antibody (Hybridoma Cell Line N. PD 08020)

ORF (SEQ ID NO: 13)

```
1    TATTGTGATC ACCCAGTCTC CAGCATCCCT GTCCATGGCT
     ATAGGAGAAA AAGTCACCAT CAGATGCATA ACCAGCACTG
     ATATTGATGA TGATATGAAC

101  TGGTACCAGC AGAAGCCAGG GGAACCTCCT AAGCTCCTTA
     TTTCAGAAGG CAATACTCTT CGTCCTGGAG TCCCATCCCG
     ATTCTCCAGC AGTGGCTATG

201  GTACAGATTT TGTTTTTACA ATTGAAAACA TGCTCTCAAA
     GATGTTGCAG ATTACTACTG TTTGCAAAGT GATAACTTGC
     CGTACACGTT CGGAGGGGGA
```

FR1: 1-76
CDR1: 77-94
FR2: 95-145
CDR2: 146-154
FR3: 155-261
CDR3: 262-300

Aminoacid sequence (SEQ ID NO: 14)

```
1    IVITQSPASL SMAIGEKVTI RCITSTDIDD DMNWYQQKPG

     EPPKLLISEG NTLRPGVPSR FSSSGYGTDF VFTIENMLSE

     DVADYYCLQS DNL
```

FR1: 1-25
CDR1: 26-31
FR2: 32-48
CDR2: 49-51
FR3: 52-87
CDR3: 88-93

VH of the 2EF Monoclonal Antibody (Hybridoma Cell Line N. PD 08021)

ORF (SEQ ID NO: 15)

```
1    CAGCTGGAGC AGTTTGGAGC TGAGCTGGTA
     AGGCCTGGGA CTTCAGTGAA GATGTCCTGC AAGGCTGCTG
     GATACACCTT CACTAACTAC TGGATAGGTT

101  GGGTAAAGCA GAGGCCTGGA CATGGCCTTG
     AGTGGATTGG AGATATTTAC CCTGGAGGTG GTTATACTAA
     CTACAATGAG AAGTTCAAGG GCAAGGCCAC

201  ACTGACTGCA GACACATCCT CCAGCACAGC
     CTACATGCAG CTCAGCAGCC TGACATTTGA GGACTTTGCC
     ATCTATTACT GTGCAAGAGG AACTGGGGGG

301  GGGGACTACT GGGGCCAAGG G
```

FR1: 1-69
CDR1: 70-93
FR2: 94-144
CDR2: 145-168
FR3: 169-282
CDR3: 283-321

Aminoacid sequence (SEQ ID NO: 16)

```
1    DVQLEQFGAE LVRPGTSVKM SCKAAGYTFT NYWIGWVKQR
     PGHGLEWIGD IYPGGGYTNY NEKFKGKATL TADTSSSTAY
     MQLSSLTFED FAIYYCARGT

101  GGGDYWGQG
```

FR1: 1-25
CDR1: 26-33
FR2: 34-50
CDR2: 51-58
FR3: 59-96
CDR3: 97-110

VL of the 2EF Monoclonal Antibody (Hybridoma Cell Line N. PD 08021)

ORF (SEQ ID NO: 17)

```
1    GATATTGTGA TGACACAGTC TCCTGCTTCC
     TTAGCTGTAT CTCTGGGGCA GAGGGCCACC ATCTCATGCA
     GGGCCAGCCA AAGTGTCAGT ACATCTAGCT

101  ATAGTTATAT GCACTGGTAC CAACAGAAAC
     CAGGACAGCC ACCCAAACTC CTCATCAAGT ATGCATCCAA
     CCTAGAATGT GGGGTCCCTG CCAGGTTCAG

201  TGGCAGTGGG TGTGGGACAG ACTTCACCCT
     CAACATCCAT CCTGTGGAGG AGGAGGATAG TGCAACATAT
     TACTGTCAGC ACAGTCGGGA GATTCCGTAC

301  ACGTTCGGAG GGGGA
```

FR1: 1-87
CDR1: 88-107
FR2: 108-159
CDR2: 160-178
FR3: 179-286
CDR3: 287-315

Aminoacid sequence (SEQ ID NO: 18)

```
1    DIVMTQSPAS LAVSLGQRAT ISCRASQSVS TSSYSYMHWY

     QQKPGQPPKL LIKYASNLEC GVPARFSGSG CGTDFTLNIH

     PVEEEDSATY YCQHSREI
```

FR1: 1-26
CDR1: 27-36
FR2: 37-53
CDR2: 53-55
FR3: 56 92
CDR3: 93-98

REFERENCES

1. Ripani, E., Sacchetti, A., Corda, D. & Alberti, S. The human Trop-2 is a tumor-associated calcium signal transducer. Int. J. Cancer 76, 671-676 (1998).
2. Calabrese, G. et al. Assignment of TACSTD1 (alias TROP1, M4S1) to human chromosome 2p21 and refinement of mapping of TACSTD2 (alias TROP2, M1S1) to human chromosome 1p32 by in situ hybridization. Cytogenet. Cell Genet. 92, 164-5 (2001).
3. Fornaro, M. et al. Cloning of the gene encoding TROP-2, a cell-surface glycoprotein expressed by human carcinomas. Int. J. Cancer 62, 610-8 (1995).
4. Alberti, S. et al. Biochemical characterization of Trop-2, a cell surface molecule expressed by human carcinomas:

formal proof that the monoclonal antibodies T16 and MOv-16 recognize Trop-2. Hybridoma 11, 539-5 (1992).

5. Fradet, Y., Cordon-Cardo, C., Whitmore, W. F., Jr., Melamed, M. R. & Old, L. J. Cell surface antigens of human bladder tumors: definition of tumor subsets by monoclonal antibodies and correlation with growth characteristics. Cancer Res 46, 5183-8 (1986).
6. Stein, R., Chen, S., Sharkey, R. M. & Goldenberg, D. M. Murine monoclonal antibodies raised against human non-small cell carcinoma of the lung: specificity and tumor targeting. Cancer Res 50, 1330-6 (1990).
7. Linnenbach, A. J. et al. Retroposition in a family of carcinoma-associated antigen genes. Mol. Cell. Biol. 13, 1507-1515 (1993).
8. Ciccarelli, F., Acciarito, A. & Alberti, S. Large and diverse numbers of human diseases with HIKE mutations. Hum. Mol. Genet. 9, 1001-7 (2000).
9. Basu, A., Goldenberg, D. M. & Stein, R. The epithelial/carcinoma antigen EGP-1, recognized by monoclonal antibody RS7-3G11, is phosphorylated on serine 303. Int. J. Cancer 62, 472-479 (1995).
10. De Vita, V. T., Hellman, S. & Rosenberg, S. A. Cancer—Principles and Practice of Oncology (eds. De Vita, V. T., Hellman, S. & Rosenberg, S. A.) (Lippincott J. B. Co., Philadelphia, 2001).
11. Velders, M. P. et al. The impact of antigen density and antibody affinity on antibody-dependent cellular cytotoxicity: relevance for immunotherapy of carcinomas. Br. J. Cancer 78, 478-483 (1998).
12. Johnson, B. E. & Janne, P. A. Rationale for a phase II trial of pertuzumab, a HER-2 dimerization inhibitor, in patients with non-small cell lung cancer. Clin Cancer Res 12, 4436s-4440s (2006).
13. Oi, V. T., Morrison, S. L., Herzenberg, L. A. & Berg, P. Immunoglobulin gene expression in transformed lymphoid cells. Proc Natl Acad Sci U S A 80, 825-9 (1983).
14. Weir, D. M., Herzenberg, L. A. & Blackwell, C. C. Handbook of experimental immunology (eds. Eds. Weir, D. M., Herzenberg, L. A. & Blackwell, C. C.) (Plenum Press, New York, 1986).
15. Alberti, S., Nutini, M. & Herzenberg, L. A. DNA methylation prevents the amplification of TROP1, a tumor associated cell surface antigen gene. Proc. Natl. Acad. Sci. USA 91, 5833-7 (1994).
16. Zanna, P. et al. Trop-1 is a novel cell growth stimulatory molecule that marks early stages of tumor progression. Cancer 110, 452-464 (2007).
17. Garofalo, A. et al. Comparative study on the metastatic behavior of human tumors in nude, beige/nude/xid and severe combined immunodeficient mice. Invasion Metastasis 13, 82-91 (1993).
18. Zhongde, W. et al. Universal PCR amplification of mouse immunoglobulin gene variable regions: the design of degenerate primers and an assessment of the effect of DNA polymerase 3' to 5' exonuclease activity. J. Immunol. Methods 233, 167-177 (2000).
19. Lefranc, M P, et al. IMGT, the international ImMunoGeneTics information system. Nucl. Acids Res. 37, 01006-1012 (2009).

The invention claimed is:

1. A combination comprising at least two isolated anti-Trop-2 monoclonal antibodies chosen among anti-Trop-2 monoclonal antibodies produced by hybridoma cell lines having deposit numbers PD 08019, PD 08020 or PD 08021.

2. The combination according to claim 1, wherein the at least two isolated anti-Trop-2 monoclonal antibodies are produced by the hybridoma cell lines having deposit numbers PD 08019, PD 08020 and PD 08021.

3. The combination according to claim 1, wherein the at least two isolated anti-Trop-2 monoclonal antibodies are produced by the hybridoma cell lines having deposit numbers PD 08019 and PD 08020.

4. The combination according to claim 1, wherein the at least two isolated anti-Trop-2 monoclonal antibodies are produced by the hybridoma cell lines having deposit numbers PD 08019 and PD 08021.

5. The combination according to claim 1, wherein the at least two isolated anti-Trop-2 monoclonal antibodies are produced by hybridoma cell lines having deposit numbers PD 08020 and PD 08021.

6. An anti-Trop-2 monoclonal antibody produced by hybridoma cell line having deposit number PD 08019.

7. An anti-Trop-2 monoclonal antibody produced by hybridoma cell line having deposit number PD 08020.

8. An anti-Trop-2 monoclonal antibody produced by hybridoma cell line having deposit number PD 08021.

9. A pharmaceutical composition comprising, as an active ingredient, the combination of claim 1, an anti-Trop-2 monoclonal antibody produced by hybridoma cell line having deposit number PD 08019, an anti-Trop-2 monoclonal antibody produced by hybridoma cell line having deposit number PD 08020, or an anti-Trop-2 monoclonal antibody produced by hybridoma cell line having deposit number PD 08021, in association with one or more excipients and/or adjuvants that are pharmaceutically acceptable.

10. The pharmaceutical composition according to claim 9 in a form acceptable for intraperitoneal, intrapleural, intravesical, intralesion administration or administration through the hepatic artery.

11. A medicament for prevention or treatment of a tumor expressing Trop-2, the medicament comprising the combination of claim 1, an anti-Trop-2 monoclonal antibody produced by hybridoma cell line having deposit number PD 08019, an anti-Trop-2 monoclonal antibody produced by hybridoma cell line having deposit number PD 08020, or an anti-Trop-2 monoclonal antibody produced by hybridoma cell line having deposit number PD 08021.

12. A medicament for prevention or treatment of Trop-2 expressing tumor metastases, the medicament comprising the combination of claim 1, an anti-Trop-2 monoclonal antibody produced by hybridoma cell line having deposit number PD 08019, an anti-Trop-2 monoclonal antibody produced by hybridoma cell line having deposit number PD 08020, or an anti-Trop-2 monoclonal antibody produced by hybridoma cell line having deposit number PD 08021.

13. A method for in vitro diagnosis of a tumor expressing Trop-2, the method comprising contacting a sample with the combination of claim 1, an anti-Trop-2 monoclonal antibody produced by hybridoma cell line having deposit number PD 08019, an anti-Trop-2 monoclonal antibody produced by hybridoma cell line having deposit number PD 08020, or an anti-Trop-2 monoclonal antibody produced by hybridoma cell line having deposit number PD 08021.

14. A kit for the in vitro diagnosis of a tumor expressing Trop-2, the kit comprising the combination of claim 1, an anti-Trop-2 monoclonal antibody produced by hybridoma cell line having deposit number PD 08019, an anti-Trop-2 monoclonal antibody produced by hybridoma cell line having deposit number PD 08020, or an anti-Trop-2 monoclonal antibody produced by hybridoma cell line having deposit number PD 08021.

15. A method for treating or preventing a tumor expressing Trop-2 in an individual, the method comprising administering to the individual an effective amount of the combination of claim 1, an anti-Trop-2 monoclonal antibody produced by hybridoma cell line having deposit number PD 08019, an anti-Trop-2 monoclonal antibody produced by hybridoma cell line having deposit number PD 08020, or an anti-Trop-2 monoclonal antibody produced by hybridoma cell line having deposit number PD 08021.

* * * * *

UNITED STATES PATENT AND TRADEMARK OFFICE

CERTIFICATE OF CORRECTION

PATENT NO. : 8,715,662 B2
APPLICATION NO. : 13/146012
DATED : May 6, 2014
INVENTOR(S) : Saverio Alberti It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 334 days.

Signed and Sealed this
Twenty-ninth Day of September, 2015

Michelle K. Lee

Michelle K. Lee
*Director of the United States Patent and Trademark Office*

SEQUENCE LISTING

```
<160> NUMBER OF SEQ ID NOS: 18

<210> SEQ ID NO 1
<211> LENGTH: 33
<212> TYPE: DNA
<213> ORGANISM: artificial
<220> FEATURE:
<223> OTHER INFORMATION: trop-2 gene forward primer

<400> SEQUENCE: 1

ccccgaattc atggctcggg gccccggcct cgc                                33


<210> SEQ ID NO 2
<211> LENGTH: 58
<212> TYPE: DNA
<213> ORGANISM: artificial
<220> FEATURE:
<223> OTHER INFORMATION: trop-2 gene reverse primer

<400> SEQUENCE: 2

ccccctctag atcacgtgat ggtgatggtg atgccccccg gtgaggcgct tcatggag      58


<210> SEQ ID NO 3
<211> LENGTH: 36
<212> TYPE: DNA
<213> ORGANISM: artificial
<220> FEATURE:
<223> OTHER INFORMATION: trop-2 gene forward primer

<400> SEQUENCE: 3

ccccgaattc taaatggctc ggggccccgg cctcgc                             36


<210> SEQ ID NO 4
```

```
<211> LENGTH: 48
<212> TYPE: DNA
<213> ORGANISM: artificial
<220> FEATURE:
<223> OTHER INFORMATION: trop-2 gene reverse primer

<400> SEQUENCE: 4

gcgaagcttt tagtgatggt gatggtgatg gcagcgtagg ctcaggtc              48


<210> SEQ ID NO 5
<211> LENGTH: 100
<212> TYPE: DNA
<213> ORGANISM: artificial
<220> FEATURE:
<223> OTHER INFORMATION: trop-2 gene forward primer

<400> SEQUENCE: 5

ccccgaattc taaatggctc ggggccccgg cctcgcgccg ccaccgctgc ggctgccgct     60

gctgctgctg gtgctggcgg cggatgagct ggtgcgcacc                         100


<210> SEQ ID NO 6
<211> LENGTH: 55
<212> TYPE: DNA
<213> ORGANISM: artificial
<220> FEATURE:
<223> OTHER INFORMATION: trop-2 gene reverse primer

<400> SEQUENCE: 6

gcgaagcttc tagtgatggt gatggtgatg ccccccggtg aggcgcttca tggag         55


<210> SEQ ID NO 7
<211> LENGTH: 330
<212> TYPE: DNA
<213> ORGANISM: artificial
<220> FEATURE:
<223> OTHER INFORMATION: ORF coding for VH region of the anti-trop-2
      monoclonal antibody produced by the ibridoma cell line  PD08019

<400> SEQUENCE: 7

cagctgcagc agtctggagc tgaggtggtg aagcgtgggg cttcagtgaa gctgtcctgc     60

aagacttctg gcttcacctt cagcagtagc tatataagtt ggttgaagca gaagcctcga    120

cagagtcttg agtggattgc atggatttat gctggaactg gtggtactag ctataatcag    180

aagttcacag gcaaggccca actgactgta gacacatcct ccagcacagc ctacatgcaa    240

ctcagcagcc tgacatctga ggactctgcc atctattact gtgcaagaca taacccttgt    300

tactatgcta tggattactg gggtcaagga                                     330


<210> SEQ ID NO 8
<211> LENGTH: 109
<212> TYPE: PRT
<213> ORGANISM: artificial
<220> FEATURE:
<223> OTHER INFORMATION: peptide sequence encoded by the ORF having
      sequence SEQ ID NO:7

<400> SEQUENCE: 8

Asp Val Gln Leu Glu Gln Phe Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
```

```
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Phe Glu Asp Phe Ala Ile Tyr Tyr Cys
                85                  90                  95

Ala Arg Gly Thr Gly Gly Gly Asp Tyr Trp Gly Gln Gly
            100                 105


<210> SEQ ID NO 9
<211> LENGTH: 301
<212> TYPE: DNA
<213> ORGANISM: artificial
<220> FEATURE:
<223> OTHER INFORMATION: ORF of the anti- trop-2 monoclonal antibody VL
      region produced by the ibridoma cell line  PD08019

<400> SEQUENCE: 9

tattgtgatc acccagtctc cagcatccct gtccatggct ataggagaaa aagtctccat      60

cagatgcata accagcactg atattgatga tgatatgaac tggtaccagc agaagccagg     120

ggaacctcct aagctcctta tttcagaagg caatactctt cgtcctggag tcccatcccg     180

attctccagc agtggctatg gtacagattt tgtttttaca attgaaaaca tgctctcaga     240

agatgttgca gattactact gtttgcaaag tgataacttg ccgtacacgt tcggaggggg     300

a                                                                     301


<210> SEQ ID NO 10
<211> LENGTH: 93
<212> TYPE: PRT
<213> ORGANISM: artificial
<220> FEATURE:
<223> OTHER INFORMATION: peptide sequence encoded by the ORF region
      having sequence SEQ ID NO:9

<400> SEQUENCE: 10

Ile Val Ile Thr Gln Ser Pro Ala Ser Leu Ser Met Ala Ile Gly Glu
1               5                   10                  15

Lys Val Ser Ile Arg Cys Ile Thr Ser Thr Asp Ile Asp Asp Asp Met
            20                  25                  30

Asn Trp Tyr Gln Gln Lys Pro Gly Glu Pro Pro Lys Leu Leu Ile Ser
        35                  40                  45

Glu Gly Asn Thr Leu Arg Pro Gly Val Pro Ser Arg Phe Ser Ser Ser
    50                  55                  60

Gly Tyr Gly Thr Asp Phe Val Phe Thr Ile Glu Asn Met Leu Ser Glu
65                  70                  75                  80

Asp Val Ala Asp Tyr Tyr Cys Leu Gln Ser Asp Asn Leu
                85                  90


<210> SEQ ID NO 11
<211> LENGTH: 330
<212> TYPE: DNA
<213> ORGANISM: artificial
<220> FEATURE:
<223> OTHER INFORMATION: ORF of the anti- trop-2 monoclonal antibody VH
      region produced by the ibridoma cell line  PD08020

<400> SEQUENCE: 11

cagctgcagc agtctggagc tgaggtggtg aagcgtgggg cttcagtgaa gctgtcctgc      60

aagacttctg gcttcacctt cagcagtagc tatataagtt ggttgaagca gaagcctcga     120

cagagtcttg agtggattgc atggatttat gctggaactg gtggtactag ctataatcag     180
```

```
aagttcacag gcaaggccca actgactgta gacacatcct ccagcacagc ctacatgcaa    240

ctcagcagcc tgacatctga ggactctgcc atctattact gtgcaagaca taacccttgt    300

tactatgcta tggattactg gggtcaagga                                     330


<210> SEQ ID NO 12
<211> LENGTH: 109
<212> TYPE: PRT
<213> ORGANISM: artificial
<220> FEATURE:
<223> OTHER INFORMATION: peptide sequence encoded by the ORF having
      sequence SEQ ID NO:11

<400> SEQUENCE: 12

Asp Val Gln Leu Glu Gln Phe Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Phe Glu Asp Phe Ala Ile Tyr Tyr Cys
                85                  90                  95

Ala Arg Gly Thr Gly Gly Gly Asp Tyr Trp Gly Gln Gly
            100                 105


<210> SEQ ID NO 13
<211> LENGTH: 300
<212> TYPE: DNA
<213> ORGANISM: artificial
<220> FEATURE:
<223> OTHER INFORMATION: ORF of the anti- trop-2 monoclonal antibody VL
      region produced by the ibridoma cell line  PD08020

<400> SEQUENCE: 13

tattgtgatc acccagtctc cagcatccct gtccatggct ataggagaaa aagtcaccat     60

cagatgcata accagcactg atattgatga tgatatgaac tggtaccagc agaagccagg    120

ggaacctcct aagctcctta tttcagaagg caatactctt cgtcctggag tcccatcccg    180

attctccagc agtggctatg gtacagattt tgtttttaca attgaaaaca tgctctcaaa    240

gatgttgcag attactactg tttgcaaagt gataacttgc cgtacacgtt cggagggggga    300


<210> SEQ ID NO 14
<211> LENGTH: 93
<212> TYPE: PRT
<213> ORGANISM: artificial
<220> FEATURE:
<223> OTHER INFORMATION: peptide sequence encoded by the ORF having
      sequence SEQ ID NO:13

<400> SEQUENCE: 14

Ile Val Ile Thr Gln Ser Pro Ala Ser Leu Ser Met Ala Ile Gly Glu
1               5                   10                  15

Lys Val Thr Ile Arg Cys Ile Thr Ser Thr Asp Ile Asp Asp Asp Met
            20                  25                  30

Asn Trp Tyr Gln Gln Lys Pro Gly Glu Pro Pro Lys Leu Leu Ile Ser
        35                  40                  45

Glu Gly Asn Thr Leu Arg Pro Gly Val Pro Ser Arg Phe Ser Ser Ser
```

```
    50                  55                  60

Gly Tyr Gly Thr Asp Phe Val Phe Thr Ile Glu Asn Met Leu Ser Glu
65                  70                  75                  80

Asp Val Ala Asp Tyr Tyr Cys Leu Gln Ser Asp Asn Leu
                85                  90


<210> SEQ ID NO 15
<211> LENGTH: 321
<212> TYPE: DNA
<213> ORGANISM: artificial
<220> FEATURE:
<223> OTHER INFORMATION: ORF of the anti- trop-2 monoclonal antibody VH
      region produced by the ibridoma cell line  PD08021

<400> SEQUENCE: 15

cagctggagc agtttggagc tgagctggta aggcctggga cttcagtgaa gatgtcctgc     60

aaggctgctg gatacacctt cactaactac tggataggtt gggtaaagca gaggcctgga    120

catggccttg agtggattgg agatatttac cctggaggtg gttatactaa ctacaatgag    180

aagttcaagg gcaaggccac actgactgca gacacatcct ccagcacagc ctacatgcag    240

ctcagcagcc tgacatttga ggactttgcc atctattact gtgcaagagg aactgggggg    300

ggggactact ggggccaagg g                                              321


<210> SEQ ID NO 16
<211> LENGTH: 109
<212> TYPE: PRT
<213> ORGANISM: artificial
<220> FEATURE:
<223> OTHER INFORMATION: peptide sequence encoded by the ORF having
      sequence SEQ ID NO:15

<400> SEQUENCE: 16

Asp Val Gln Leu Glu Gln Phe Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Phe Glu Asp Phe Ala Ile Tyr Tyr Cys
                85                  90                  95

Ala Arg Gly Thr Gly Gly Gly Asp Tyr Trp Gly Gln Gly
            100                 105


<210> SEQ ID NO 17
<211> LENGTH: 315
<212> TYPE: DNA
<213> ORGANISM: artificial
<220> FEATURE:
<223> OTHER INFORMATION: ORF of the anti- trop-2 monoclonal antibody VL
      region produced by the ibridoma cell line  PD08021

<400> SEQUENCE: 17

gatattgtga tgacacagtc tcctgcttcc ttagctgtat ctctggggca gagggccacc     60

atctcatgca gggccagcca aagtgtcagt acatctagct atagttatat gcactggtac    120

caacagaaac caggacagcc acccaaactc ctcatcaagt atgcatccaa cctagaatgt    180
```

-continued

```
ggggtccctg ccaggttcag tggcagtggg tgtgggacag acttcaccct caacatccat    240

cctgtggagg aggaggatag tgcaacatat tactgtcagc acagtcggga gattccgtac    300

acgttcggag gggga                                                     315


<210> SEQ ID NO 18
<211> LENGTH: 98
<212> TYPE: PRT
<213> ORGANISM: artificial
<220> FEATURE:
<223> OTHER INFORMATION: peptide sequence encoded by the ORF having
      sequence SEQ ID NO:17

<400> SEQUENCE: 18

Asp Ile Val Met Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Cys Gly Val Pro Ala
    50                  55                  60

Arg Phe Ser Gly Ser Gly Cys Gly Thr Asp Phe Thr Leu Asn Ile His
65                  70                  75                  80

Pro Val Glu Glu Glu Asp Ser Ala Thr Tyr Tyr Cys Gln His Ser Arg
                85                  90                  95

Glu Ile
```